April 26, 1966 R. L. BYRUM Plant Pat. 2,626
ROSE PLANT
Filed March 9, 1965
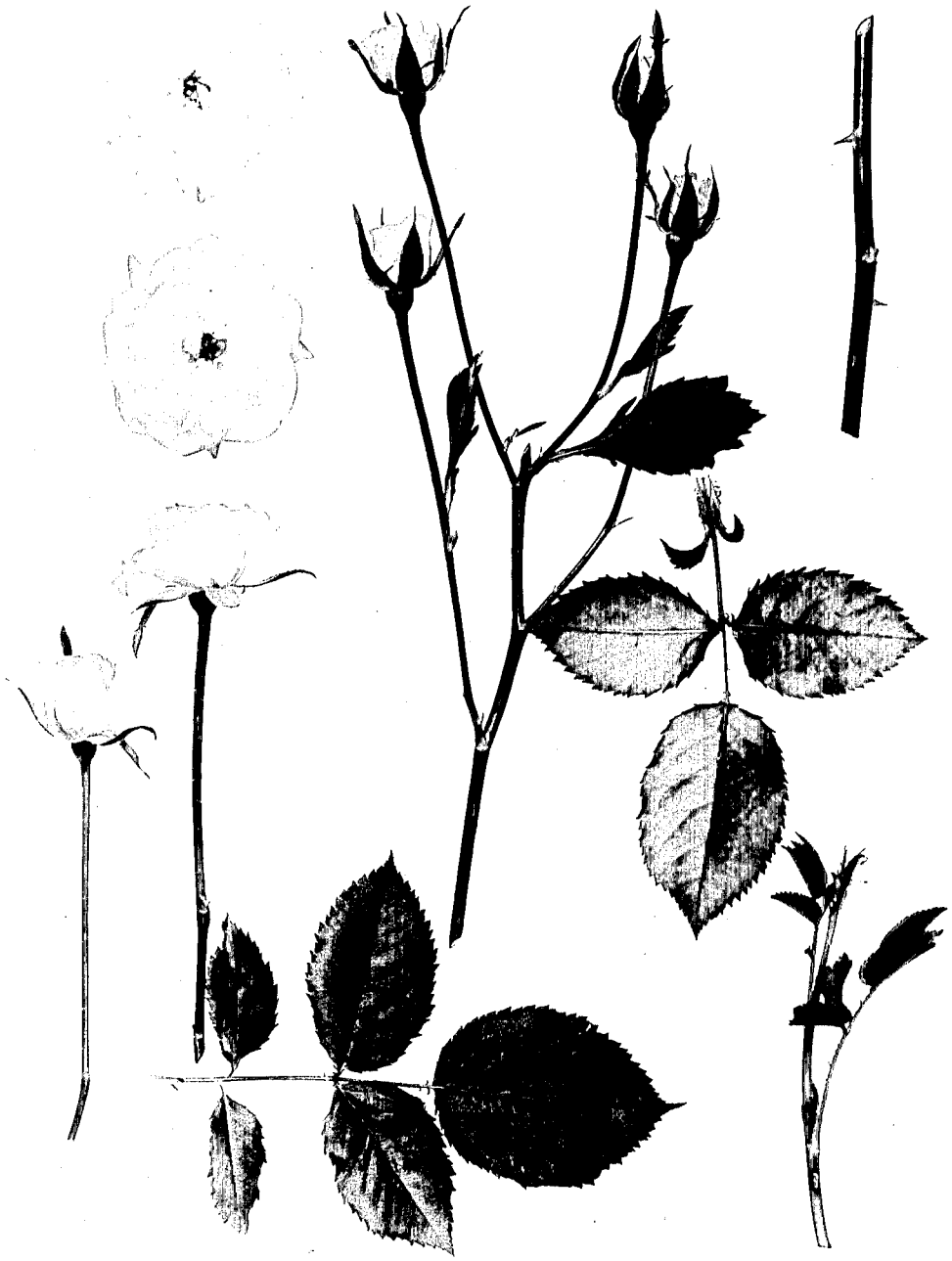
Inventor
Roy L. Byrum
By: Robb & Robb
Attorneys.

United States Patent Office

Plant Pat. 2,626
Patented Apr. 26, 1966

2,626
ROSE PLANT

Roy L. Byrum, Richmond, Ind., assignor to Joseph H. Hill Company, Richmond, Ind., a corporation of Indiana Filed Mar. 9, 1965, Ser. No. 438,439
1 Claim. (Cl. Plt.—22)

The present invention relates to a new and distinct variety of rose plant of the floribunda class, which was originated by me by crossing an unnamed and unpatented seedling derived from a cross of another unnamed and unpatented seedling × "Garnette Supreme" (Plant Patent No. 1,318) with the variety "Rumba" (Plant Patent No. 1,919).

The primary objective of this breeding was to produce a new and improved variety of rose plant having the good foliage and the good flower keeping qualities of the pollen parent "Rumba," but characterized by better flower production when grown in greenhouses during winter months. This objective was fully achieved, along with other desirable improvements, as evidenced by the following characteristics which are outstanding in the new variety and which distinguish it from its parents, as well as from all other varieties of which I am aware:

(1) Abundant, medium size and attractive foliage;
(2) Good flower keeping qualities;
(3) Good flower production when grown in greenhouses during winter months; and
(4) An unusual range of flower colors beginning as a deep Orange Yellow color in the bud stage and then progressing through lighter shades of yellow to various shades of pink at maturity.

The unnamed seed parent of my new variety was a red flowered floribunda type having the characteristic of vigorous growth. The new variety is considered to be an improvement over this parent variety because it combines the vigorous growth characteristic of the seed parent with an unusual flower color range.

As compared with its pollen parent "Rumba," the new variety achieves better flower production in greenhouses, especially during the winter months, and it also produces larger and more colorful flowers which are borne on longer stems and are therefore more suitable for cut flower purposes.

Asexual reproduction of my new variety by grafting, as performed at Richmond, Indiana, and also by budding, as performed at Wills Point, Texas, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)), and Koster's Color Guide (hereinafter abbreviated as (K)), except where general color terms of ordinary dictionary significance are obvious:

Type: Bush; seedling.
Class: Floribunda.
Breeding: Seedling.
*Seed parent.*—An unnamed red flowered floribunda seedling.
*Pollen parent.*—"Rumba."
Propagation: Holds its distinguishing characteristics through succeeding propagations by both budding and grafting.

*Flower*

Locality where grown and observed: Richmond, Indiana.
Flowers borne: From singly to 3 or 4 to stem; in irregular clusters; on short, strong stems.
Quantity of bloom: Abundant, in greenhouse.
Continuity: Continuous, in greenhouse.
Fragrance: Slight, in greenhouse.
Bud:
*Peduncle.*—Medium length; small diameter; strong; erect. Bark—smooth. Color—Scheeles Green, Plate 860/1 (W). Thorns—none. Prickles—numerous; color—near Uranium Green, Plate 63/3 (W). Hairs—none.
*Before calyx breaks.*—Size—small. Form—short pointed; ovoid; with a conspicuous neck; with foliaceous appendages on the surface of the bud; with much cut foliaceous parts extending beyond the tip of the bud equal to ½ or more of its length. Color—Scheeles Green, Plate 860/2 (W).
*As calyx breaks.*—Color (outside of petal)—mostly Mimosa Yellow, Plate 602 (W), changing to Crimson Red, Plate 28 (K) at top of petal.
*As first petal opens.*—Size—medium small. Form—short pointed; ovoid. Color—outside—Aureolin, Plate 3/2 (W), with upper portion usually shaded with Fire Red, Plate 21 (K); inside—Aureolin, Plate 3/1 (W) at base, changing to Fire Red, Plate 21 (K) at top of petals.
*Opening.*—Opens well in greenhouse.
Bloom:
*Size (when fully open).*—Small; from about 2 inches to 2½ inches.
*Petalage.*—Very double; from 45 to 50 petals; arranged regulary.
*Form.*—Full and high-centered at first, but becoming flat; petals being at first very tightly rolled outward, but later becoming loosely rolled outward at maturity.
Petals:
*Texture.*—Thick; leathery.
*Appearance.*—Inside—satiny. Outside—satiny.
*Shape.*—Outer petals—obovate, with apex obtuse. Intermediate petals—obovate, with apex obtuse. Inner petals—obovate, with apex retuse and with one notch.

This description of a newly opened flower was made from a rose grown in a greenhouse during the month of February at Richmond, Indiana:

*Color.*—Outer petal—outside surface—Barium Yellow, Plate 503 (W) over lower portion, changing to Spiraea Red, Plate 025/2 (W) at top of petal; inside surface—Lemon Yellow, Plate 4/1 (W) over lower portion, changing to Geranium Lake, Plate 20/2 (W) at top of petal. Intermediate petal—outside surface—Chrome Yellow, Plate 605 (W) with upper portion margined with Delft Rose, Plate 020/2 (W); inside surface—Lemon Yellow, Plate 4 (W), with upper portion overlaid with Brick Red, Plate 016 (W). Inner petal—outside surface—Chrome Yellow, Plate 605 (W); inside surface—Lemon Yellow, Plate 4 (W), with upper portion lightly washed with Nasturtium Orange, Plate 610 (W).

This description was made from a rose that was open for three days in a greenhouse during the month of February at Richmond, Indiana:

*Color.*—Outer petal—outside surface—Dresden Yellow, Plate 64/3 (W), with varying amounts of Spiraea Red, Plate 025/1 (W) toward top of petal; inside surface—Dresden Yellow, Plate 64/2 (W) at base, gradually changing to Dresden Yellow, Plate 64/3 (W), with top of petal overlaid with Neyron Rose, Plate 623 (W). Intermediate petal—outside surface—Dresden Yellow, Plate 64/3 (W) over lower portion, gradually fading to almost White at top; inside surface—Dresden Yellow, Plate 64/2 (W) at base, gradually changing to Dresden Yellow, Plate 64/3 (W), with top of petal overlaid with Neyron Rose, Plate 623/1 (W). Inner petal—outside surface—Dresden Yellow, Plate 64/2 (W) at base, gradually changing through Dresden Yellow, Plate 64/3 (W) to almost White at top; inside surface—Dresden Yellow, Plate 64/1 (W) at base, gradually changing through Dresden Yellow, Plate 64/2 (W) to Dresden Yellow, Plate 64/3 (W), with top overlaid with Begonia, Plate 619/1 (W).

*General color effect.*—Newly opened flower—Cadmium Orange, Plate 8/2 (W). Three days open—Dawn Pink, Plate 523/1 (W).

*Behavior.*—Persist in greenhouse.

*Flower longevity.*—Cut roses grown in greenhouse and kept at living room temperatures—5 or 6 days in February.

*Plant*

Foliage:

*Leaves.*—Compound of 5–7 leaflets; abundant; medium large; moderately heavy.

*Leaflets.*—Shape—ovoid. Apex—acute. Base—round. Margin—simply serrate.

*Color.*—Mature—upper surface—near Spinach Green, Plate 0960 (W). Under surface—near Cedar Green, Plate 80 (K). Young—upper surface—Fern Green, Plate 0862/1 (W), edged with Purple Madder, Plate 1028/3 (W) and washed with tints of Purple Madder, Plate 1028/3 (W) over most of surface; under surface—Fern Green, Plate 0862/2 (W), with some leaves lightly washed with tints of Purple Madder, Plate 1028/3 (W).

*Rachis (the supporting stem of the compound leaf).*—Medium, heavy. Upper side—grooved. Under side—smooth; prickly.

*Stipules.*—Moderately long and narrow; with points of medium length turning out at an angle of less than 45°.

Growth (in greenhouse):

*Habit.*—Bush; upright; much branched.

*Growth.*—Vigorous.

*Canes.*—Medium diameter.

*Main stems.*—Color—Spinach Green, Plate 75 (K), with some streaks of Van Dyck Brown, Plate 96 (K). Thorns—several; medium length; hooked downward; with short, narrow base; color—Van Dyck Brown, Plate 96 (K). Prickles—none. Hairs—none.

*Branches.*—Color—Scheeles Green, Plate 860 (W). Thorns—several; medium length; hooked downward; with long narrow base; color—near Uranium Green, Plate 63/3 (W). Prickles—none. Hairs—none.

*New shoots.*—Color—Moss Green, Plate 76 (K). Thorns—several; medium length; hooked downward; with long, round base. Color—Erythrite Red, Plate 0027/1 (W) at base, gradually changing through Erythrite Red, Plate 0027/2 (W) and through Erythrite Red, Plate 0027/3 (W) to Chartreuse Green, Plate 663/2 (W). Prickles—none. Hairs—none.

*Reproductive organs*

Stamens: Many; arranged regularly about pistils.

Filaments: Medium length; most with anthers. Color—Lemon Yellow, Plate 4/2 (W).

Anthers: Small; all open at once. Color—Mimosa Yellow, Plate 602/2 (W) at center, with edging of Red Ochre, Plate 94 (K).

Pollen: Abundant. Color—Chinese Yellow, Plate 606 (W).

Pistils: Many.

Styles: Uneven; medium length; moderately thin; bunched. Color—Chartreuse Green, Plate 663/3 (W).

Stigma: Color—Mimosa Yellow, Plate 602/2 (W).

Ovularies: Some protruding from calyx.

Hips: None.

Sepals: Permanent; long; straight; curled.

*Color.*—Inside—Fern Green, Plate 0862 (W), overlaid with White fuzz. Outside—Fern Green, Plate 0862 (W).

Seeds: None.

I claim:

A new and distinct variety of rose plant of the floribunda class, substantially as herein shown and described, characterized particularly as to novelty by the unique combination of abundant, medium size and attractive foliage, good flower keeping qualities, good flower production when grown in greenhouses during winter months, and an unusual range of flower colors beginning as a deep Orange Yellow color in the bud stage and then progressing through lighter shades of yellow to various shades of pink at maturity.

No references cited.

ANTONIO F. GUIDA, *Acting Primary Examiner.*

R. E. BAGWILL, *Assistant Examiner.*

Dedication

Plant Pat. No. 2,626.—*Roy L. Byrum*, Richmond, Ind. ROSE PLANT. Patent dated Apr. 26, 1966. Dedication filed Sept. 21, 1971, by the assignee, *Joseph H. Hill Company*.

Hereby dedicates its entire interest in the said patent to the Public of the United States.

[*Official Gazette November 9, 1971.*]